(12) United States Patent
Guillemin et al.

(10) Patent No.: US 10,842,810 B2
(45) Date of Patent: Nov. 24, 2020

(54) CONTINUOUS RELEASE COMPOSITIONS MADE FROM HYALURONIC ACID, AND THERAPEUTIC APPLICATIONS OF SAME

(71) Applicant: GENBIOTECH, Antibes (FR)

(72) Inventors: Yannis Guillemin, Villeneune Loubet (FR); Dominique Vacher, Mougins (FR); Thomas Perrier, Saint-Barthelemy D'anjou (FR); Maud Gonnet, Angers (FR); Jean-Noël Gouze, Vallauris (FR)

(73) Assignee: GENBIOTECH, Antibes (FR)

( * ) Notice: Subject to any disclaimer, the term of this patent is extended or adjusted under 35 U.S.C. 154(b) by 0 days.

(21) Appl. No.: 14/909,909

(22) PCT Filed: Aug. 6, 2014

(86) PCT No.: PCT/IB2014/063744
§ 371 (c)(1),
(2) Date: Feb. 3, 2016

(87) PCT Pub. No.: WO2015/019304
PCT Pub. Date: Feb. 12, 2015

(65) Prior Publication Data
US 2016/0175342 A1 Jun. 23, 2016

(30) Foreign Application Priority Data
Aug. 9, 2013 (WO) ............... PCT/EP2013/066763

(51) Int. Cl.
| | |
|---|---|
| *A61K 31/728* | (2006.01) |
| *A61K 9/00* | (2006.01) |
| *A61K 8/73* | (2006.01) |
| *A61K 8/85* | (2006.01) |
| *A61K 8/86* | (2006.01) |
| *A61K 9/16* | (2006.01) |
| *A61Q 19/08* | (2006.01) |

(52) U.S. Cl.
CPC ............ *A61K 31/728* (2013.01); *A61K 8/735* (2013.01); *A61K 8/86* (2013.01); *A61K 9/0019* (2013.01); *A61K 9/0024* (2013.01); *A61K 9/1641* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 5,972,906 A | 10/1999 | Asculai et al. | |
| 6,004,573 A * | 12/1999 | Rathi | A61K 9/0024 |
| | | | 424/426 |
| 6,197,326 B1 * | 3/2001 | Suzuki | A61K 9/5031 |
| | | | 424/426 |
| 7,067,144 B2 † | 6/2006 | Demopulos | |
| 7,456,275 B2 | 11/2008 | Shimoboji | |
| 7,582,311 B1 * | 9/2009 | Cleland | A61K 9/0019 |
| | | | 424/488 |
| 2005/0164980 A1 * | 7/2005 | Shimoboji | A61K 31/728 |
| | | | 514/54 |
| 2006/0040894 A1 * | 2/2006 | Hunter | A61K 31/19 |
| | | | 514/54 |
| 2006/0140988 A1 | 6/2006 | Chen et al. | |
| 2008/0124400 A1 | 5/2008 | Liggins et al. | |
| 2010/0316683 A1 | 12/2010 | Piron et al. | |
| 2012/0282298 A1 * | 11/2012 | Bodick | A61K 9/0019 |
| | | | 424/400 |

FOREIGN PATENT DOCUMENTS

| | | |
|---|---|---|
| EP | 0911025 | 4/1999 |
| WO | 9625168 | 8/1996 |
| WO | 03041685 A1 | 5/2003 |
| WO | 2006071694 | 7/2006 |

(Continued)

OTHER PUBLICATIONS

Hedberg et al.; "Controlled release of hyaluronan oligomers from biodegradable polymeric microparticle carriers," 2004, Elsevier, Journal of Controlled Release, vol. 100, pp. 257-266.*
Odian, George; Principles of Polymerization, 4th ed., Wiley-Interscience, 2004, pp. 1-38.*
Tran et al.; "Protein-loaded PLGA-PEG-PLGA microspheres: A tool for cell therapy," 2012, Elsevier, European Journal of Pharmaceutical Sciences, vol. 45, pp. 128-137. (Year: 2012).*
Mäder; "RESOMER®—Biodegradable Polymers for Sutures, Medical Devices, Drug Delivery and Tissue Engineering," 2012, SIGMA ALDRICH, pp. 62-66. (Year: 2012).*
Makadia et al.; "Poly Lactic-co-Glycolic Acid (PLGA) as Biodegradable Controlled Drug Delivery Carrier," 2011, MDPI AG, Polymers, vol. 3, pp. 1377-1397. (Year: 2011).*

(Continued)

*Primary Examiner* — David J Blanchard
*Assistant Examiner* — Ivan A Greene
(74) *Attorney, Agent, or Firm* — Hamre, Schumann, Mueller & Larson, P.C.

(57) ABSTRACT

The present invention concerns polymer particles made from poly(lactic-co-glycolic acid) (PLGA) polymer, poly(lactic-co-glycolic acid)-polyethylene glycol-poly(lactic-co-glycolic acid) (PLGA-PEG-PLGA) copolymer, or the mixture of same, combined with hyaluronic acid molecules or hyaluronic acid salts, and the method for preparing same. The present invention also concerns injectable pharmaceutical or cosmetic compositions comprising such polymer particles, the method for preparing such compositions, and the use thereof for medical purposes, in particular for the prevention and/or treatment of musculoskeletal diseases, diseases and traumatic conditions of the skin, oral disorders, vaginal mucosa dryness and urinary infections or cystitis, dryness of the eye membrane and eye infections, obesity, and the use of same to combat ageing of the skin and/or for repairing the dermal tissue (mesotherapy).

13 Claims, 4 Drawing Sheets

(56) References Cited

FOREIGN PATENT DOCUMENTS

Figure 2:
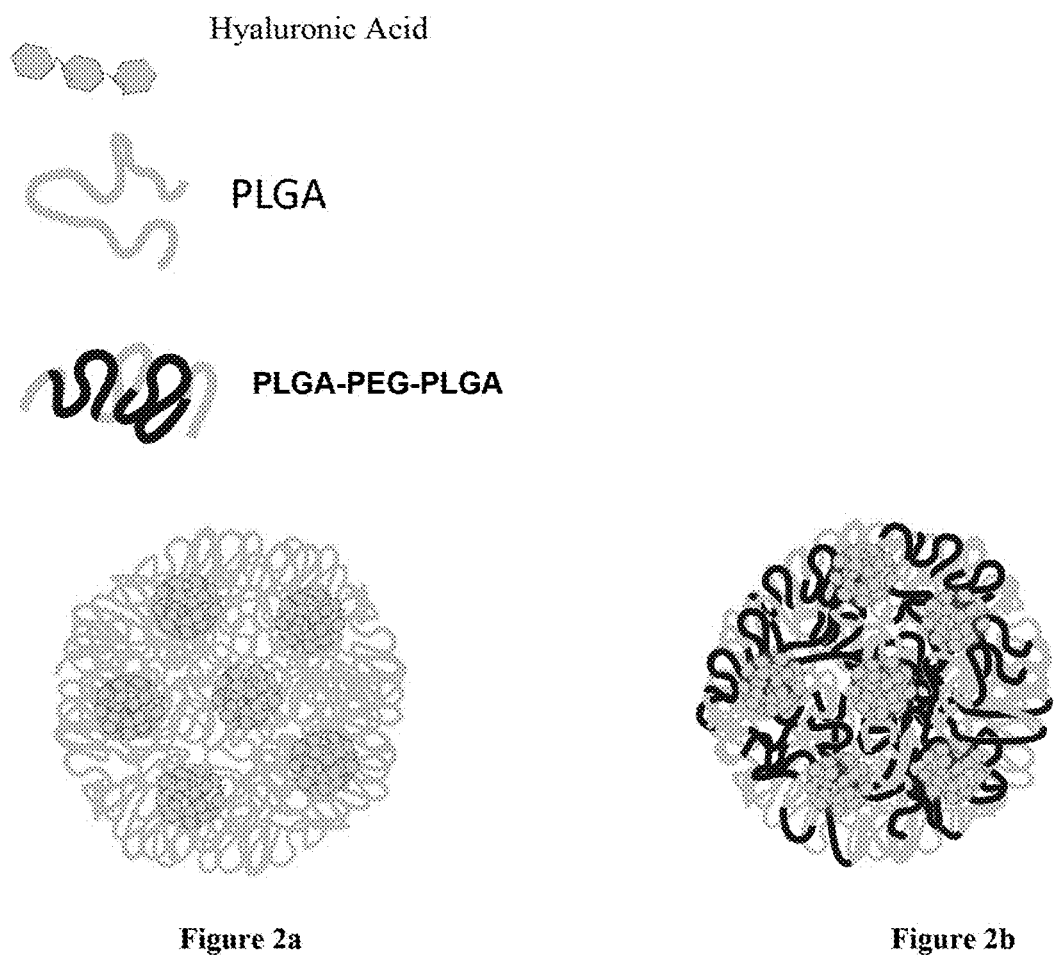

| WO | 2008068297 | 6/2008 |
| WO | 2008147817 | 12/2008 |
| WO | 2012093753 | 7/2012 |

OTHER PUBLICATIONS

International Search Report issued in International Application No. PCT/IB2014/063744 dated Feb. 2, 2015 (3 pages).
Yadaz et al.: "Development and characterisation of hyaluronic acid—anchored PLGA nanoparticulate carriers of doxorubicin"; Nanomedicine: Nanotechnology, Biology, and Medicine, 2007, vol. 3, pp. 246-257.
Ponta et al.: "CD44: From adhesion molecules to signaling regulators"; Nature Review, Molecular Cell Biology, 2003, vol. 4, pp. 33-45.
Ando et al.: "Intra-articular Injection of Hyaluronan Diminishes Loss of Chondrocytes in a rat Immobilized-Knee Model"; Tohoku J. Exp. Med., 2008, pp. 231-331.
Zhou et al.: "The effect of hyaluronic Acid on IL-1b-Induced Chondrocyte Apoptosis in a Rat Model of Osteoarthritis"; Journal of Orthopaedic Research, 2008, pp. 1643-1648.
Vignon et al.: "Les marqueurs biologiques de la destruction du cartilage articulaire: aspects actuels"; Recherche et therapeutiques dans l'arthrose, La revue du Practicien (Paris), 1997, pp. 11-15.
Mendoza et al.: "Antioxidant Prile of Hyaluronan: Physico-Chemical Features and its Role in Pathologies"; Mini-Reviews in Medicinal Chemistry, 2009, vol. 9, pp. 1479-1488.
Nagaoka et al.: "Biological Activities of Glucosamine and Its related Substances"; Advances in Food and Nutrition Research, 2012, vol. 65, Chap. 22, pp. 338-350.
Li et al.: "Hyaluronan injection in murine osteoarthritis prevents TGFbeta 1-induced synovial neovascularization and fibrosis and maintains articular cartilage integrity by a CD44-dependent mechanism"; Arthritis Research and Therapy, 2012, 14:R151, pp. 1-16.
F. Masson: "Acide Hyaluronique et hydratation cutanee"; Annales de dermatologie, 2010, vol. 137, pp. 23-25.
Hargittai et al.: "Molecular structure of hyaluronan: an introduction"; Struct. Chem., 2008, vol. 19, pp. 697-717.
Bellamy et al.: Viscosupplementation for the treatment of osteoarthritis of the knee (Review); The Cochrane Collaboration, Jonh Wiley & Sons, 2006, pp. 1-627.
De Boulle et al.: "A review of the Metabolism of 1,4-Butanediol Diglycidyl Ether-Crosslinked Hyaluronic Acid Dermal Fillers"; Dermatologic Surgery, 2013, vol. 39, pp. 1758-1766.
Schante et al.: "Chemical modification sof hyaluronic acid for the synthesis of derivatives for a broad range of biomedical applications"; Carbohydrate Polymers, 2011, vol. 85, pp. 469-489.
Mongkhon et al.: "Sorbitol-modified hyaluronic acid reduces oxidative stress, apoptosis and mediators of inflammation and catabolism in human osteoarthritic chondrocytes"; Inflammation Research, Springer, 2014, pp. 1-11.
S. Van et al.: "Traitement de la cystite interstitielle par instillation intravesicale d'acide hyaluronique: etude prospective sur 31 patientes"; Progres en urologie, 2011, vol. 21, pp. 218-225.
Gerwin et al.: "Intraarticular drug delivery in osteoarthritis"; Advanced Drug Delivery Reviews, 2006, vol. 58, pp. 226-242.
Fagnola et al.: "Hyaluronic acid in hydrophilic contact lenses: Spectroscopic investigation of the content and release in solution"; Contact Lens & Anterior Eye, 2009, vol. 32, pp. 108-112.
Langeslay et al.: "Glycosaminoglycans: Oligosaccharide Analysis by Liquid Chromatography, Capillary Electrophoresis, and Specific Labeling"; Proteoglycans: Methods and Protocols, Methods in Molecular Biology, 2012, vol. 836, Chapter 9, pp. 131-143.
Patel, R. B. et al., "Characterization of formulation parameters affecting low molecular weight drug release from in situ forming drug delivery systems," J Biomed Mater Res A. Aug. 2010; 94(2): 476-484.
Hedberg, Elizabeth L., et al. "Controlled release of hyaluronan oligomers from biodegradable polymeric microparticle carriers." Journal of controlled release 100.2 (2004): 257-266.†

\* cited by examiner
† cited by third party

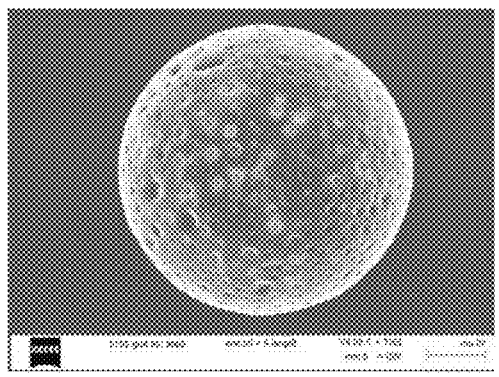 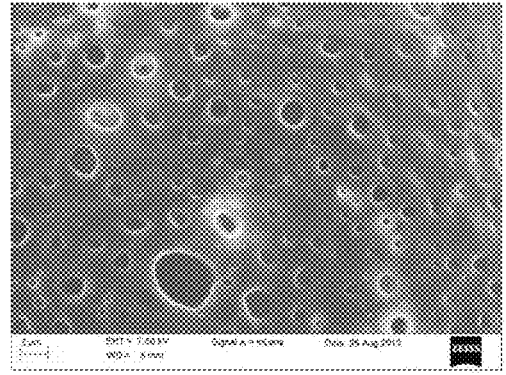
FIGURE 1a
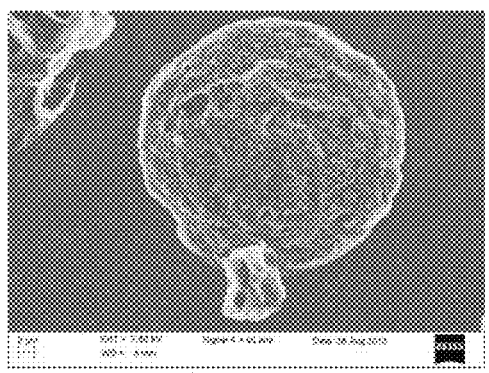 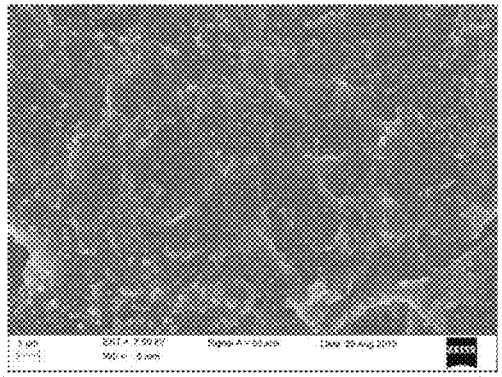
FIGURE 1b
FIGURE 1

CONTINUOUS RELEASE COMPOSITIONS MADE FROM HYALURONIC ACID, AND THERAPEUTIC APPLICATIONS OF SAME

The present invention relates to polymer particles based on poly(lactic-co-glycolic acid) (PLGA) polymer, on poly(lactic-co-glycolic acid)-polyethylene glycol-poly(lactic-co-glycolic acid) (PLGA-PEG-PLGA) copolymer or on their mixture, combined with molecules of hyaluronic acid or of hyaluronic acid salts, and to their process of preparation. Another subject matter of the present invention is injectable pharmaceutical or cosmetic compositions comprising such polymer particles, the process for preparation of such compositions and their use as medicament, in particular for the prevention and/or treatment of musculoskeletal disorders, of diseases and traumatic states of the skin, of oral conditions, of dryness of the vaginal mucous membrane and urinary infections or cystitis, of dryness of the ocular membrane and ocular infections, and of obesity, and also to their use in combating aging of the skin and/or in repairing dermal tissue (mesotherapy). More particularly, the compositions of the invention can be intended to supplement joint fluids, in particular synovial fluid, by reestablishing the physiological and rheological conditions of the pathological joint, for example osteoarthritic joint, or also for caring for and repairing the epidermis by remodeling, hydrating and protecting the skin. Finally, the invention is targeted at a kit consisting of two containers, one at least of which comprises polymer particles according to the invention, and is also targeted at a ready-for-use syringe comprising a composition according to the invention.

Osteoarthritis is characterized by disability and loss of motricity. The joints concerned are firstly the knee but also the shoulder, the cervical vertebrae and the hip. Local intra-articular injections of hyaluronic acid can be used therapeutically in viscosupplementation against these painful osteoarthritic phenomena (such as effusion-free osteoarthritis of the knee).

Injections of hyaluronic acid also occupy an important place in cosmetics for treating physiological aging of the skin or trauma of the skin, by providing for the repair of the tissues.

The main advantage of injectable compositions based on hyaluronic acid lies in the maintenance of all of the properties of hyaluronic acid, namely:
at the cellular and biochemical level, antiapoptotic properties (Ponta H. et al., Nature Reviews, Molecular Cell Biology, 2003, Vol. 4, 33-45; Ando A. et al., Tohoku J. Exp. Med., 2008, 215, 321-331; Zhou P H et al., Journal of Orthopaedic Research, 2008, 1643-1648), antiinflammatory properties (Vignon et al., 1997, 47, S11-S15; Ando A. et al., 2008; Zhou P H et al., Journal of Orthopaedic Research, 2008, 1643-1648), antioxidant properties (Mendoza G. et al., Mini-Reviews in Medicinal Chemistry, 2009, 9, 1479-1488), properties with regard to improving the synthesis of hyaluronic acid by synoviocytes (Nagaoka I. et al., Advances in Food and Nutrition Research, 2012, Vol. 65, Chap. 22), antifibrotic properties (Li J. et al., Arthritis Research & Therapy, 2012, 14:R151), and moisturizing properties (Masson, F., Annales de dermatologie, 2010, 137, Supplément 1, S23-S25; Hargittai I. et al., Struct. Chem., 2008, 19, 697-717),
at the biomechanical level: viscosupplementation (Bellamy N. et al., Viscosupplementation for the treatment of osteoarthritis of the knee (Review), 2006, The Cochrane Collaboration®, John Wiley & Sons).

In pathologies of the joint, injectable hyaluronic acid solutions are effective and well tolerated pharmaceutical tools. These solutions prevent rapid decomposition of the hyaluronic acid and prolong its effectiveness at the point of injection. This results in a marked improvement in the functionality of the joints over a prolonged period of time. Furthermore, hyaluronic acid is perfectly well tolerated in the joint and does not exhibit immunogenicity.

Currently, injections of hyaluronic acid require an injection rate of one to five injections, via the joint or subcutaneously, at an interval of one week. They exhibit an effect in the case of the joint which does not exceed 6 to 8 months in effectiveness. In addition, even if the injection of noncrosslinked hyaluronic acid produces a rapid effect in desensitizing the joints, it is found that, on average, after 24 h, there no longer remains any trace of hyaluronic acid at the site of the injection.

U.S. Pat. No. 7,456,275 B2 describes a pharmaceutical preparation of low viscosity composed of hyaluronic acid bonded by chemical modification to a block polymer, this preparation exhibiting a prolonged antalgic effect. The method employed to manufacture such a preparation exhibits the disadvantage of modifying the chemical structure of the hyaluronic acid active principle by creation of strong covalent bonds between the hyaluronic acid and the polymer. In addition, the hyaluronic acid thus chemically modified is not soluble in an aqueous medium but only in organic media, such as dimethyl sulfoxide. Thus, it is necessary to prepare an emulsion in a mineral oil before injection, the addition of such a solvent partially denaturing the active principle.

Application WO 2006/071694 describes an emulsion of hyaluronic acid combined with a biodegradable polymer used as viscosupplementation product for improving joint pain. The hyaluronic acid is present in droplets dispersed in an organic polymer phase, the use of organic solvents and surfactants possibly proving to be harmful. The method of preparation of such an emulsion also shows problems of reproducibility insofar as the size of the droplets formed cannot be controlled. Finally, another disadvantage of this method lies in the need for storage under cold conditions for several days, once the emulsion has been prepared.

The Inventors have now developed a process for the preparation of polymer particles combined with hyaluronic acid molecules or hyaluronic acid salts which makes it possible to overcome the disadvantages of the compositions described in the prior art. The compositions comprising the polymer particles of the invention exhibit a slower release profile for hyaluronic acid than the compositions of the prior art (prolonged diffusion of the hyaluronic acid over time), the duration of availability of the hyaluronic acid consequently being longer. The composition of the invention has a continuous effect over time, which reduces the frequency of the joint injections, it being possible for the compositions of the invention to be injected just once in a year. The hyaluronic acid combined with the polymer particles is then diffused as small doses, over several months, as if a continuous "infusion" of hyaluronic acid, for example into the joint, was concerned, significantly reducing the number of injections. In addition, the composition of the invention exhibits the advantage of being a stable sterile freeze-dried composition which can be used in just one syringe, in contrast to the composition of Application WO 2006/071694.

Thus, a first subject matter of the present invention is polymer particles composed of at least a poly(lactic-co-glycolic acid) (PLGA) polymer, a poly(lactic-co-glycolic acid)-polyethylene glycol-poly(lactic-co-glycolic acid) (PLGA-PEG-PLGA) copolymer or their mixture, combined with hyaluronic acid molecules or hyaluronic acid salts.

The structure of the PLGA polymer is represented below:

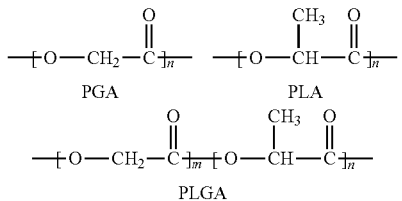

The hyaluronic acid of the invention can exist either in a crosslinked form or in a noncrosslinked form. The crosslinked hyaluronic acid consists of two or more molecules of hyaluronic acid joined to one another via covalent bonds, thus forming a cohesive and stable gelled mass of hyaluronic acid (De Boulle K. et al., Dermatologic Surgery, 2013, 39, 1758-1766; Schanté C. E. et al., Carbohydrate Polymers, 85, 2011, 469-489). Preferably, the hyaluronic acid of the invention exists in a noncrosslinked form.

When the hyaluronic acid molecules are provided in the form of salts, they are preferably sodium salts.

The hyaluronic acid molecules or hyaluronic acid salts are preferably combined with the poly(lactic-co-glycolic acid)-polyethylene polymer and/or with the poly(lactic-co-glycolic acid)-polyethylene glycol-poly(lactic-co-glycolic acid) copolymer via low-energy bonds and preferably via hydrogen bonds and/or Van der Waals bonds. This is because the process for the preparation of the polymer particles of the invention makes it possible to combine the hyaluronic acid molecules with the poly(lactic-co-glycolic acid) (PLGA) polymer, with the polylactic-co-glycolic acid)-polyethylene glycol-poly(lactic-co-glycolic acid) (PLGA-PEG-PLGA) copolymer or with their mixture without chemical modification of the structure of the hyaluronic acid, that is to say without formation of covalent bonds between the hyaluronic acid and the polymer. Thus, the process of the invention avoids the use of activating agents and coupling agents, such as hydrazine, normally necessary to modify the structure of the hyaluronic acid and to create covalent bonds (Schanté C. E. et al., Carbohydrate Polymers, 85, 2011, 469-489).

According to a preferred embodiment, the polymer particles of the invention are composed of a mixture of poly(lactic-co-glycolic acid) (PLGA) polymer and of poly(lactic-co-glycolic acid)-polyethylene glycol-poly(lactic-co-glycolic acid) (PLGA-PEG-PLGA) copolymer. Advantageously, the ratio by weight of the poly(lactic-co-glycolic acid) (PLGA) polymer to the poly(lactic-co-glycolic acid)-polyethylene glycol-poly(lactic-co-glycolic acid) (PLGA-PEG-PLGA) copolymer varies from 40/60 to 60/40 and is preferably 50/50.

According to an even more preferred embodiment, the polymer particles of the invention consist solely of poly(lactic-co-glycolic acid)-polyethylene glycol-poly(lactic-co-glycolic acid) (PLGA-PEG-PLGA) copolymer (100% PLGA-PEG-PLGA).

The polyethylene glycol (PEG) preferably has a high molecular weight ranging from 4 000 to 10 000 g·mol$^{-1}$. The PLGA preferably has a molecular weight ranging from 54 000 to 69 000 g·mol$^{-1}$. The poly(lactic-co-glycolic acid)-polyethylene glycol-poly(lactic-co-glycolic acid) (PLGA-PEG-PLGA) copolymer preferably has a molecular weight ranging from 50 000 to 70 000 g·mol$^{-1}$. These polymers are available commercially, for example under the references LSB 5050 DLG/PEG 6000 and Resomer RG 505 from Evonik.

The polymer particles of the invention preferably have a size ranging from 10 to 130 µm and more preferably ranging from 20 to 85 µm. The size of the particles can be determined by polydispersity according to the particle size distribution using a Multisizer® 3 Coulter counter (Beckman Coulter).

The hyaluronic acid molecules or hyaluronic acid salts combined with the polymer particles for their part preferably have a molecular weight which can vary from $0.8 \times 10^6$ to $1.2 \times 10^6$ g·mol$^{-1}$, for example determined by size exclusion chromatography (SEC) or high performance liquid chromatography (HPLC), the hyaluronic acid molecules or hyaluronic acid salts available commercially having a molecular weight varying from $0.5 \times 10^6$ to $6.0 \times 10^6$ g·mol$^{-1}$.

Advantageously, the content by weight of hyaluronic acid or of hyaluronic acid salts combined with the polymer particles varies from 1 to 50 µg·mg$^{-1}$, preferably from 5 to 30 µg·mg$^{-1}$ and more preferably still from 10 to 30 µg·mg$^{-1}$.

Another subject matter of the invention is a process for the preparation of polymer particles as defined according to the invention, said process comprising the following stages:

(i) with stirring, emulsifying an aqueous solution of hyaluronic acid or of hyaluronic acid salts in an organic solution comprising at least a poly(lactic-co-glycolic acid) (PLGA) polymer, a poly(lactic-co-glycolic acid)-polyethylene glycol-poly(lactic-co-glycolic acid) (PLGA-PEG-PLGA) copolymer or their mixture, (ii) with stirring, mixing the emulsion obtained from stage (i) with an aqueous solution of polyvinyl alcohol (PVA), (iii) with stirring, adding an aqueous solvent to the emulsion obtained from stage (ii), said aqueous solvent employed preferably being purified water, (iv) filtering the emulsion obtained from stage (iii), in order to remove the aqueous phase, (v) freeze-drying the polymer particles obtained from stage (iv), this stage making it possible to remove the traces of water possibly present in the polymer particles obtained from stage (iv), (vi) optionally sterilizing the freeze-dried polymer particles obtained from stage (v).

During stage (i), the aqueous solution of hyaluronic acid or of hyaluronic acid salts can be based on purified water and optionally on polyvinyl alcohol (PVA); preferably, an aqueous solution of polyvinyl alcohol (PVA) having a concentration by weight of polyvinyl alcohol (PVA) of 1 to 10%, preferably of 2 to 5% and more preferably still of 4% is involved. The poly(lactic-co-glycolic acid) (PLGA) polymer and/or the poly(lactic-co-glycolic acid)-polyethylene glycol-poly(lactic-co-glycolic acid) (PLGA-PEG-PLGA) copolymer is preferably in solution in an organic solvent chosen from dichloromethane, acetone or their mixture. Stage (i) is preferably carried out with stirring using a stirrer of Ultra-Turrax® type or a source of ultrasound. Stage (i) can be carried out at room temperature and then under cold conditions in an ice bath.

The aqueous solution of polyvinyl alcohol (PVA) employed during stage (ii) preferably has a concentration by weight of polyvinyl alcohol (PVA) of 1 to 10%, advantageously of 2 to 5% and more advantageously still of 4%. Said polyvinyl alcohol (PVA) preferably has a molecular weight ranging from 30 000 to 50 000 g·mol$^{-1}$. The ratio by volume of the aqueous solution of polyvinyl alcohol (PVA) to the emulsion obtained from stage (i) advantageously varies between 20/1 and 40/1.

During stage (ii), the emulsion obtained from stage (i) can be injected, using a syringe, into a reactor, preferably into a homogenizer of Silverson type or a reactor having cylindrical symmetry, comprising the aqueous solution of polyvinyl alcohol (PVA). Stirring can be maintained for 1 to 10 minutes, before adding an aqueous solvent to the emulsion (stage (iii)). Stirring can subsequently be again maintained for 5 to 15 minutes, in order for the solvent present in the droplets formed to diffuse into the aqueous solution containing the polyvinyl alcohol (PVA) and to result in the combination of the hyaluronic acid with the polymer particles. Optionally, the solvent present in the emulsion obtained from stage (iii) can subsequently be evaporated, before being filtered according to stage (iv).

Preferably, the filtration stage (iv) is carried out on a hydrophilic filter, such as HVLP 0.45 μm or SSWP 3 μm filters.

After stage (iv), the polymer particles obtained can be washed with purified water.

After this optional washing stage, the polymer particles obtained can be packaged in a flask or a syringe, before being freeze-dried.

According to a preferred embodiment, after this packaging stage, the polymer particles according to the invention can be brought into contact with an uptake solution comprising a pharmaceutically or cosmetically acceptable excipient and/or another active principle (other than hyaluronic acid), this solution being added to the polymer particles obtained from stage (iv) and after the optional washing stage, before freeze-drying. The uptake solution of the invention can be purified water, a buffered aqueous solution of hyaluronic acid (crosslinked or noncrosslinked) or of hyaluronic acid salts, or an aqueous solution of another salt, such as sodium chloride (NaCl), it being possible for said uptake solution to also comprise, depending on the final application targeted, one or more solvents chosen from ethanol, propylene glycol, polyethylene glycol, squalene, vegetable oils, such as oils based on mono-, di- or triglycerides, mineral oils or cod liver oil. This uptake solution is preferably an isotonic solution, the nature of which depends on the final application targeted. For example, it can be an aqueous solution of noncrosslinked hyaluronic acid or of hyaluronic acid salts when the final application is targeted at preventing and/or treating osteoarthritis; an aqueous solution of crosslinked hyaluronic acid for the filling of wrinkles; or an aqueous solution of sodium chloride (NaCl) for mesotherapy. Advantageously, the uptake solution employed after stage (iv), and optionally after the packaging stage, is purified water optionally comprising sorbitol, mannitol or trehalose, preferably sorbitol, as pharmaceutically acceptable excipient, and an anesthetic agent, as active principle.

The expression "pharmaceutically or cosmetically acceptable excipient" denotes diluents, adjuvants or vehicles, such as preservatives, fillers, disintegrating agents, wetting agents, emulsifying agents, suspending agents, solvents, dispersants, lubricants, coatings, antibacterial and antifungal agents, isotonic agents, absorption delaying agents and their analogs. The pharmaceutically or cosmetically acceptable excipient of the invention is preferably chosen from sorbitol, mannitol, trehalose or lactose, and preferably sorbitol. Other pharmaceutically or cosmetically suitable excipients can be envisaged depending on the final application targeted, for example in order to modify the color or the taste of the composition of the invention, if the latter is intended for oral use.

The additional active principle can be an anesthetic agent, such as lidocaine.

Some pharmaceutically acceptable excipients, such as sorbitol, can act both as pharmaceutically acceptable excipient and as additional active principle, said sorbitol exhibiting, in addition to its role of excipient, anti-inflammatory properties (trapper of free radicals) (Mongkhon J-M. et al., Inflamm. Res., Springer, 2014).

The freeze-drying stage (v) is advantageously carried out according to the following cycle:
decreasing the temperature to a temperature of −38° C. over a period of time ranging from 30 minutes to 1 h 30,
increasing the temperature to a temperature ranging from −38° C. to +15° C. over a period of time ranging from 1 h 30 to 2 h 30,
drying at a temperature of +15° C. for a period of time ranging from 4 to 6 h,
increasing the temperature to a temperature ranging from +15 to +25° C. over a period of time ranging from 15 to 45 minutes, then
drying at a temperature of +25° C. for a period of time of 8 to 12 h.

The freeze-dried polymer particles can subsequently be sterilized by sterilization with gamma rays during a stage (vi). This type of sterilization makes it possible to prevent any deterioration in the structure and any detrimental change in the properties of the polymer particles obtained.

A composition, preferably a pharmaceutical or cosmetic composition, comprising polymer particles as defined according to the invention constitutes another subject matter of the invention. In such a composition, the polymer particles are in suspension in an uptake solution as defined above, it being possible for said uptake solution to be identical to or different from that used after the washing stage carried out after stage (iv). Advantageously, the uptake solution present in the composition of the invention is purified water, a buffered aqueous solution of hyaluronic acid (crosslinked or noncrosslinked) or of hyaluronic acid salts, or an aqueous solution of another salt, such as sodium chloride (NaCl). More preferably still, the uptake solution present in the composition of the invention is a buffered aqueous solution of hyaluronic acid (crosslinked or noncrosslinked) or of hyaluronic acid salts, preferably at a concentration by weight of hyaluronic acid or of hyaluronic acid salts ranging from 0.5 to 10% and preferably from 0.5 to 4%.

According to an advantageous embodiment, the composition of the invention can also comprise a pharmaceutically or cosmetically acceptable excipient as defined above. According to another advantageous embodiment, the composition of the invention can also comprise another active principle. Said additional active principle is as defined above.

The invention also relates to a process for the preparation of a composition as defined according to the invention, said process comprising stages (i) to (vi) as defined above and a stage (vii) of suspending the freeze-dried polymer particles obtained from stage (v) or (vi) in an uptake solution as defined above, it being possible for said uptake solution to also comprise a pharmaceutically or cosmetically acceptable excipient and/or another active principle. Advantageously, the uptake solution employed during stage (vii) is purified water, a buffered aqueous solution of hyaluronic acid (crosslinked or noncrosslinked) or of hyaluronic acid salts, or an aqueous solution of another salt, such as sodium chloride (NaCl). More preferably still, the uptake solution employed during stage (vii) is a buffered aqueous solution of hyaluronic acid (crosslinked or noncrosslinked) or of hyaluronic acid salts, preferably at a concentration by weight of hyaluronic acid or of hyaluronic acid salts ranging from 0.5 to 10% and preferably from 0.5 to 4%.

Another subject matter of the present invention is a composition according to the invention for use thereof as medicament and preferably in the prevention and/or treatment of musculoskeletal disorders, diseases and traumatic states of the skin, such as burns, oral conditions, dryness of the vaginal mucous membrane and urinary infections, ocular infections and obesity, during the insertion of gastric-bands, and also in the prevention and/or treatment of rheumatological diseases in animals and more particularly racehorses.

More particularly, the subject matter of the invention is the prevention and/or treatment:
- of musculoskeletal disorders, such as osteoarthritis and more particularly osteoarthritis of the knee or effusion-free osteoarthritis,
- oral conditions chosen from dryness of the oral mucous membranes (WO 2012/093753 A1), inflammation and traumatic states of the oral mucous membrane,
- dryness of the vaginal mucous membrane and urinary infections or cystitis (WO 1996/025168 A1; EP 0813417 A1; S. Van Agt et al., Progrès en urologie, Vol. 21, Issue 3, 2011, pp. 218-225), and
- dryness of the ocular membrane and ocular infections.

The composition of the invention can also be used to combat aging of the skin and/or for repairing dermal tissue (mesotherapy).

Finally, the invention relates to a kit comprising:
(a) a first container comprising polymer particles as defined according to the invention, and
(b) a second container comprising an uptake solution as defined above, it being possible for said uptake solution to also comprise a pharmaceutically or cosmetically acceptable excipient and/or another active principle as defined above.

According to an advantageous embodiment of the kit of the invention, more particularly intended for the prevention and/or treatment of musculoskeletal disorders, the first container is a bottle or a syringe and the second container is a syringe, said containers being connected to one another via a suitable connector.

Thus, the compositions of the invention can be presented either in a single injection module or in two parts (kit) and, in the latter case, be mixed at the time of use, before injection in situ, either by the intra-articular route, for the treatment of the joints, or by the subcutaneous route, for the repair of the skin.

A final subject matter of the invention is targeted at a ready-for-use syringe comprising a composition as defined according to the invention. Such a syringe is particularly suitable for cosmetic use, for example for caring for and repairing the epidermis by remodeling or moisturizing.

Figure 3:
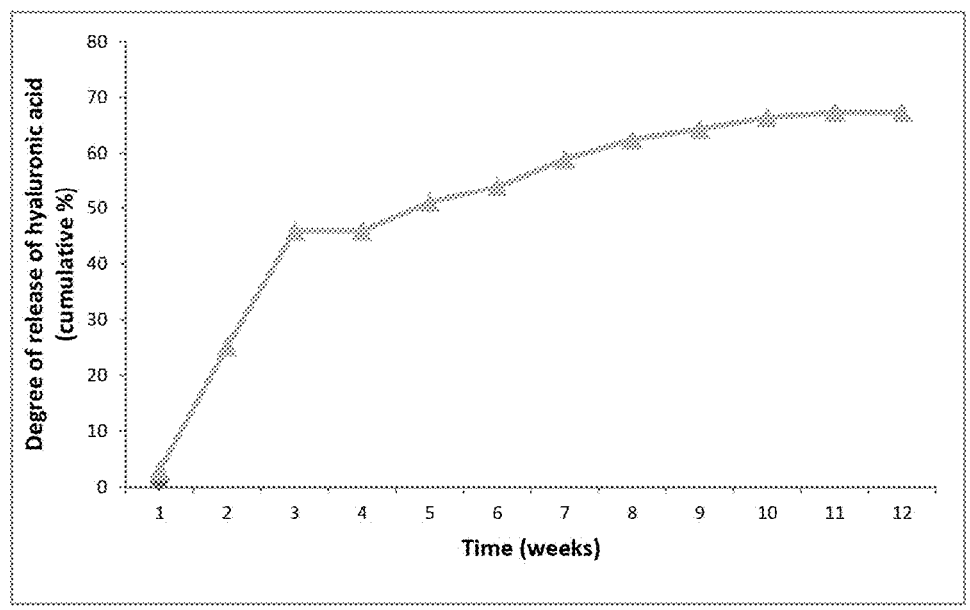
Figure 4:
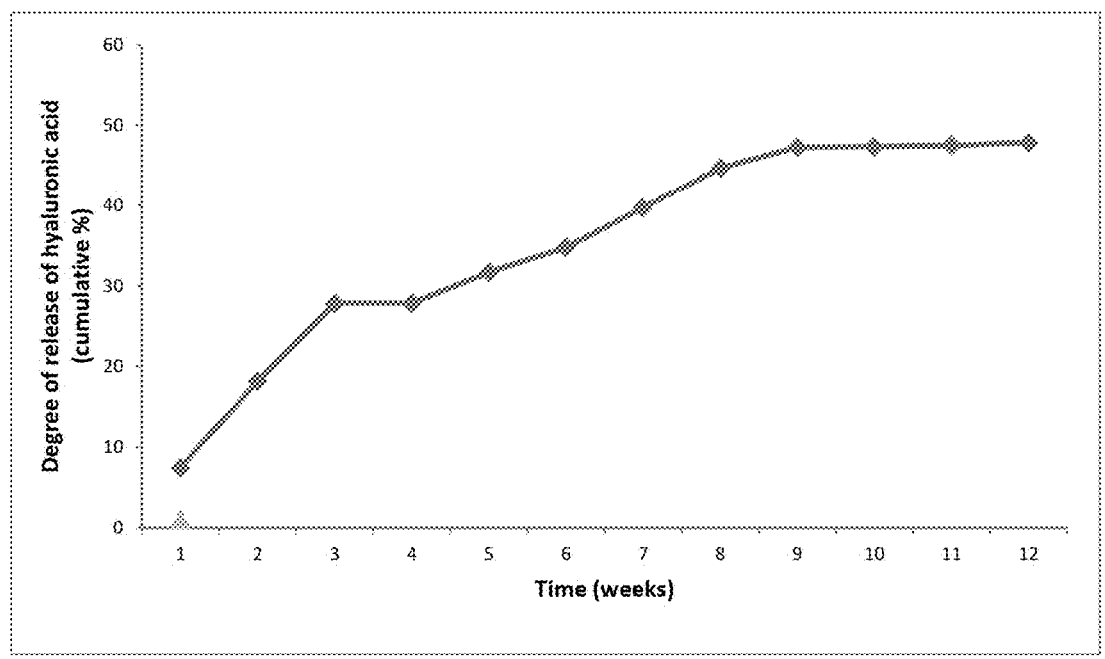

In addition to the preceding provisions, the invention also comprises other provisions which will emerge from the remainder of the description which follows, which relates to examples of preparations of polymer particles and of compositions according to the invention and to the in vivo evaluation of the tolerance of these compositions during injections into the intraarticular space of rabbits, and also to the appended drawings, in which:

FIGS. 1a and 1b are respectively images of polymer particles in which are bonded hyaluronic acid molecules according to the invention prepared according to example 1 and example 2 (scanning electron microscopy images), FIGS. 2a and 2b respectively represent PLGA polymer particles according to the invention combined with hyaluronic acid molecules (FIG. 2a) and PLGA-PEG-PLGA polymer particles according to the invention combined with hyaluronic acid molecules (FIG. 2b), FIG. 3 represents the release profile of the polymer particles combined with hyaluronic acid molecules prepared according to example 1, and FIG. 4 represents the release profile of the polymer particles combined with hyaluronic acid molecules prepared according to example 2.

EXAMPLES

Starting materials used:

TABLE 1

| Reactants | Commercial references | Suppliers |
| --- | --- | --- |
| Hyaluronic acid | AH HMW | Altergon |
| Polyvinyl alcohol (PVA) | Gohsenol EG-05PW | Nippon Gohsei |
| PLGA-PEG-PLGA triblock | LSB 5050 DLG PEG 6000 | Evonik (Birmingham Labs) |
| PLGA | Resomer RG 505 | Evonik |
| Ultrapure water | — | MilliPore |
| Acetone | 24201 | Sigma-Aldrich |
| Dichloromethane | 24233 | Sigma-Aldrich |
| Sorbitol | S1876 | Sigma-Aldrich |

Example 1

Preparation of the Polymer Particles According to the Invention $1^{st}$ Stage: "Primary" Emulsification An aqueous solution of hyaluronic acid is prepared by dissolving 50 mg of hyaluronic acid in 5 ml of a 4% by weight polyvinyl alcohol (PVA) solution. An organic solution of polymer is also prepared by dissolving 900 mg of a PLGA-PEG-PLGA triblock polymer in 12 ml of a dichloromethane/acetone (3/1 v/v) mixture. These two solutions are emulsified at room temperature for two minutes with a stirrer of Ultra-Turrax® IKA T25 Basic type at a speed of 16 000 revolutions/minute and simultaneously with magnetic stirring using a magnetic bar at a speed of 500 revolutions/minute. A second stirring cycle is carried out in identical fashion in an ice bath.

$2^{nd}$ Stage: "Secondary" Emulsification

The stable emulsion obtained from the $1^{st}$ stage is introduced into a glass syringe and then injected into a formulation reactor containing 450 ml of 4% by weight polyvinyl alcohol (PVA), with magnetic stirring at a rate of 750 revolutions/minute.

$3^{rd}$ Stage: Addition of an Aqueous Solvent

Stirring is maintained for two minutes and then 500 ml of ultrapure water (resistivity greater than 18 MΩ·cm$^{-1}$) are added to the reactor. Stirring is subsequently maintained for an additional ten minutes, at a rate of 750 revolutions/minute. The solvent present in the preformed droplets is then diffused into the aqueous phase containing the polyvinyl alcohol (PVA) and polymer particles combined with hyaluronic acid molecules are then formed.

$4^{th}$ Stage: Purification and Extraction of the Solvent

The solvent present in the emulsion obtained from the $3^{rd}$ stage is subsequently evaporated by magnetic stirring at a rate of 500 revolutions/minute for 4 h at 20° C. in a fume cupboard.

The polymer particles charged with hyaluronic acid are subsequently filtered on an SSWP 3 µm hydrophilic filter in order to remove the aqueous phase. The particles obtained are subsequently washed with ultrapure water in a proportion of 3 l per 900 mg of particles.

The polymer particles are subsequently packaged in flasks made of amber glass with a height of 50 mm and a diameter of 24 mm (150 mg of particles per flask). The particles are subsequently covered with 1 ml of ultrapure water per 150 µg of polymer particles.

5$^{th}$ Stage: Freeze-Drying and Sterilization

The polymer particles present in the flasks are subsequently freeze-dried in order to obtain a lyophilizate of dry particles. The freeze-drying is carried out according to the following cycle: decreasing the temperature to a temperature of −38° C. over 1 h, then increasing the temperature from −38° C. to +15° C. over 2 h, followed by drying at +15° C. for 5 h, then increasing the temperature from +15° C. to +25° C. over 30 min, followed by drying at +25° C. for 10 h.

The freeze-dried particles charged with hyaluronic acid are subsequently sterilized by irradiation with gamma radiation at 15 kGy.

6$^{th}$ Stage:

150 mg of polymer particles are dissolved in 1 ml of a sterile aqueous solution comprising 2 ml of NaCl in which 16 mg of hyaluronic acid are dissolved. Dissolution is carried out with a Luer-Lock® syringe system.

Analysis of the Polymer Particles of the Invention According to Example 1:

The analyses were carried out on 10 batches of polymer particles according to the invention. The results obtained are as follows:

size of the particles obtained by polydispersity according to the particle size analysis using a Multisizer® 3 Coulter counter (Beckman Coulter): 66.34 µm±3.6 µm (before irradiation) and 65.34 µm±7.09 µm (after irradiation), a content of hyaluronic acid charge of 13 µg of hyaluronic acid per mg of freeze-dried polymer particles, and a combination yield of the hyaluronic acid molecules with the polymer particles of approximately 40%.

The results obtained are summarized in table 2 (size of the particles charged with hyaluronic acid, combination yield of the hyaluronic acid molecules with the polymer particles and content of hyaluronic acid charge in the particles).

Results:

The release profile of the polymer particles bonded to hyaluronic acid molecules prepared according to example 1 is represented in FIG. 3. The measurements were carried out in a biomimetic medium, a medium similar to synovial fluid (medium devoid of proteins having a viscosity identical to that of synovial fluid) being reconstituted according to N. Gerwin et al., Advanced Drug Delivery Reviews, 2006, 58, 226-242 (assaying once per week for 12 weeks, with cumulative results on each occasion). The polymer particles of the invention were added to this medium at 37° C. with stirring and then centrifuged in order to recover the hyaluronic acid released and to assay the hyaluronic acid released by the Stain-All assaying method (colorimetric assaying of the Stain-All complex at 460 nm) (Fagnola M. et al., Contact Lens & Anterior Eye, 2009, 108-112; Langeslay D. J. et al., Proteoglycans: Methods and Protocols, Methods in Molecular Biology, Vol. 836, Chap. 9, pp. 131-143). In order to extract an assay with hyaluronic acid, 10 mg of polymer particles according to the invention are mixed for 30 seconds with 2 ml of $CH_2Cl_2$ under stirring of vortex type (Vortex-Genie 2, Scientific Industries, Bohemia, N.Y., USA), left to stand for 5 min, before the addition of 2 ml of water under stirring of vortex type, left to stand for 30 min and then centrifuged at a speed of 3500 revolutions/min at 4° C. for 5 min (Jouan Thermo CR3 centrifuge). 150 µl of the aqueous phase recovered are mixed for 30 seconds with 1.850 ml of water at a pH of 7.4 under stirring of vortex type (Vortex-Genie 2, Scientific Industries, Bohemia, N.Y., USA). A Stain-All solution (1 ml) is subsequently added to the medium and assaying is carried out at an absorbance of 640 nm with a UV-visible spectrophotometer using a hyaluronic acid calibration curve.

Evaluations of in vivo tolerance were also carried out on a pharmaceutical composition prepared according to example 1. This composition is injected into the intraarticular space of rabbits and the effect on the synovial membrane and on the synovial fluid was studied. Quantitative and semiquantitative analyses of the tissue effects were carried out according to Standard ISO 10993-6 on different circulating cells of the immune system. The results obtained with

TABLE 2

| | | Mean size (µm) | | Combination yield of the hyaluronic acid molecules with the polymer particles (%) | | Content of charge (µg/mg) | |
|---|---|---|---|---|---|---|---|
| | | Before irradiation | After irradiation | Before irradiation | After irradiation | Before irradiation | After irradiation |
| Batches | 1 | 65.87 | 61.74 | 50 | 51 | 16.20 | 16.53 |
| | 2 | 72.13 | 73.45 | 57 | 55 | 18.47 | 17.82 |
| | 3 | 62.54 | 65.89 | 57 | 52 | 18.47 | 16.85 |
| | 4 | 64.58 | 70.87 | 40 | 38 | 12.96 | 12.31 |
| | 5 | 61.32 | 58.44 | 29 | 27 | 9.40 | 8.75 |
| | 6 | 67.12 | 69.78 | 29 | 28 | 9.40 | 9.07 |
| | 7 | 71.45 | 76.44 | 40 | 38 | 12.96 | 12.31 |
| | 8 | 69.63 | 62.77 | 42 | 40 | 13.61 | 12.96 |
| | 9 | 63.82 | 55.23 | 37 | 36 | 11.99 | 11.67 |
| | 10 | 64.97 | 58.75 | 35 | 38 | 11.34 | 12.31 |
| Mean | | 66.34 | 65.34 | 41.60 | 40.30 | 13.48 | 13.06 |
| Standard deviation | | 6.69 | 7.09 | 10.18 | 9.60 | 3.30 | 3.11 |

Images of polymer particles combined with hyaluronic acid molecules according to the invention prepared according to example 1 are represented in FIG. 1a.

regard to the synovial membrane are presented in table 3 and those obtained with regards to the synovial fluid are presented in table 4.

TABLE 3

Score of the effect of the injection of the polymer particles
according to the invention with regard to the synovial membrane
0: Absent; 1: Slight; 2: Moderate; 3: Marked; 4; Severe

| Injected product | Polymer particles obtained according to example 1 | | PBS | Sinovial ® | Polymer particles obtained according to example 1 | | PBS | Sinovial ® |
|---|---|---|---|---|---|---|---|---|
| Injection volume | 0.4 ml | | | | 0.4 ml | | | |
| Concentration of the product | 150 mg of particles*/ml | 15 mg of particles*/ml | — | 8 mg of hyaluronic acid/ml | 150 mg of particles*/ml | 15 mg of particles*/ml | — | 8 mg of hyaluronic acid/ml |
| mg of hyaluronic acid administered | 1.5 | 0.15 | — | 3.2 | 1.5 | 0.15 | — | 3.2 |
| *(25 µg of hyaluronic acid/mg of particles) | | | | | | | | |
| Day post-injections | | D3 | | | | D7 | | |
| Polymorphonuclear cells | 2 | 0.7 | 0 | 0 | 1 | 0.3 | 0 | 0 |
| Lymphocytes | 0.7 | 0 | 0 | 0 | 0.3 | 0 | 0 | 0 |
| Plasmocytes | 0 | 0 | 0 | 0 | 0 | 0 | 0 | 0 |
| Macrophages | 2 | 1.3 | 0 | 1 | 1.3 | 0.7 | 0 | 0 |
| Giant multinucleated cells | 1.7 | 1.3 | 0 | 0 | 1.3 | 0.3 | 0 | 0 |
| Overall score/4 | 1.28 | 0.66 | 0 | 0.2 | 0.78 | 0.26 | 0 | 0 |
| Visual appearance of the membrane | 0.3 | 0 | 0 | 0 | 0 | 0 | 0 | 0 |
| Necrosis | 0.3 | 0 | 0 | 0 | 0 | 0 | 0 | 0 |
| Fibrosis | 2 | 1.3 | 1 | 0 | 1.3 | 1 | 0 | 0 |
| Neovascularization | 2 | 1.3 | 0 | 0 | 1.3 | 1 | 0 | 0 |
| Lipid vesicle | 0 | 0 | 0 | 0 | 0 | 0 | 0 | 0 |
| Fibrin | 2 | 1 | 0 | 0 | 1.3 | 0.3 | 0 | 0 |
| Degeneration | 1.3 | 0.7 | 0 | 0 | 1 | 0.3 | 0 | 0 |
| Hyperplasia | 1.7 | 1.7 | 0 | 0 | 2 | 1 | 0 | 0 |
| Hypertrophy | 2 | 1.7 | 0 | 1 | 2 | 1.3 | 0 | 1 |
| Erosion | 2 | 1.3 | 0 | 0 | 1.7 | 0.3 | 0 | 0 |

These results show that the injected composition according to the invention is well tolerated by the synovial membrane of the joint of rabbits. At the highest dose, the slight inflammatory effect observed on the 3$^{rd}$ day disappears on the 7$^{th}$ day.

Macroscopic measurements of the inflammation of the knee joint of rabbits were subsequently carried out, at the point where the composition according to the invention was injected. The thickness of the joint with respect to day 0 (D0) was measured using a Vernier caliper. The "macroscopic edema measurements (%/D0)" presented in table 5 below represent the increase as % in the volume of the edema with respect to D0.

TABLE 4

Score of the effect of the injection of the polymer particles
according to the invention with regard to the synovial fluid
0: Absent; 1: Slight; 2: Moderate; 3: Marked; 4: Severe

| Injected product | Polymer particles obtained according to example 1 | | PBS | Sinovial ® | Polymer particles obtained according to example 1 | | PBS | Sinovial ® |
|---|---|---|---|---|---|---|---|---|
| Injection volume | 0.4 ml | | | | 0.4 ml | | | |
| Concentration of the product | 150 mg of particles*/ml | 15 mg of particles*/ml | — | 8 mg of hyaluronic acid/ml | 150 mg of particles*/ml | 15 mg of particles*/ml | — | 8 mg of hyaluronic acid/ml |
| mg of hyaluronic acid administered | 1.5 | 0.15 | — | 3.2 | 1.5 | 0.15 | — | 3.2 |
| *(25 µg of hyaluronic acid/mg of particles) | | | | | | | | |
| Day post-injections | | D3 | | | | D7 | | |
| Polymorphonuclear cells | 1 | 1.3 | 0 | 0 | 0.3 | 0 | 0 | 0 |
| Lymphocytes | 0.7 | 0.7 | 0 | 1 | 0.7 | 0 | 0 | 0 |
| Plasmocytes | 0 | 0 | 0 | 0 | 0 | 0 | 0 | 0 |
| Macrophages | 1.7 | 1.3 | 0 | 1 | 0.7 | 0.5 | 0 | 1 |
| Giant multinucleated cells | 0 | 0 | 0 | 0 | 0 | 0 | 0 | 0 |
| Overall score/4 | 0.68 | 0.66 | 0 | 0.4 | 0.34 | 0.1 | 0 | 0.2 |
| Fibrin | 0 | 0 | 0 | 0 | 0 | 0 | 0 | 0 |
| Red blood cells | 1 | 1 | 0 | 0 | 0.3 | 0.5 | 0 | 1 |
| Synovial cells | 2 | | 1 | 1 | 1 | 1 | 1 | 1 |

These results show that the injected composition according to the invention is well tolerated with regard to the synovial fluid of rabbits.

TABLE 5

| | Macroscopic edema measurement (%/D0) | | | | | | | |
|---|---|---|---|---|---|---|---|---|
| Injected product | Polymer particles obtained according to example 1 | | PBS | Sinovial ® | Polymer particles obtained according to example 1 | | PBS | Sinovial ® |
| Injection volume | 0.4 ml | | | | 0.4 ml | | | |
| Concentration of the product | 150 mg of particles*/ml | 15 mg of particles*/ml | — | 8 mg of hyaluronic acid/ml | 150 mg of particles*/ml | 15 mg of particles*/ml | — | 8 mg of hyaluronic acid/ml |
| mg of hyaluronic acid administered | 1.5 | 0.15 | — | 3.2 | 1.5 | 0.15 | — | 3.2 |
| *(25 µg of hyaluronic acid/mg of particles) | | | | | | | | |
| Day post-injections | | D3 | | | | D7 | | |
| Macroscopic edema measurement (%/D0) | 1.00 | 1.00 | N.D. | 1.02 | 1.02 | 1.02 | N.D. | 1.03 |

N.D.: not determined

These results show that the injected composition according to the invention is well tolerated with regard to the knee joint of rabbits and does not cause macroscopic edema.

Example 2

Preparation of the Polymer Particles According to the Invention

A similar process to that of example 1 is employed to prepare polymer particles according to the invention. The only variation which was made with respect to the process of example 1 is the preparation of a "secondary" emulsion during the 2$^{nd}$ stage using a Silverson stirrer at a speed of 2800 revolutions/minute, in place of magnetic stirring at 750 revolutions/minute in example 1.

Analysis of the Polymer Particles of the Invention According to Example 2:

The analyses were carried out on 10 batches of polymer particles according to the invention. The results obtained are as follows:

- size of the particles obtained by polydispersity according to the particle size analysis using a Multisizer® 3 Coulter counter (Beckman Coulter): 34.98 µm±7.02 µm (before irradiation) and 34.12 µm±7.23 µm (after irradiation),
- a content of hyaluronic acid charge of 16 µg of hyaluronic acid per mg of freeze-dried polymer particles, and
- a combination yield of the hyaluronic acid molecules with the polymer particles of approximately 20%.

The results obtained are summarized in table 6 (size of the particles charged with hyaluronic acid, combination yield of the hyaluronic acid molecules with the polymer particles and content of hyaluronic acid charge in the particles).

TABLE 6

| | | Mean size (µm) | | Combination yield of the hyaluronic acid molecules with the polymer particles (%) | | Content of charge (µg/mg) | |
|---|---|---|---|---|---|---|---|
| | | Before irradiation | After irradiation | Before irradiation | After irradiation | Before irradiation | After irradiation |
| Batches | 1 | 35.54 | 31.45 | 29 | 27 | 23.72 | 22.09 |
| | 2 | 37.62 | 32.56 | 20 | 21 | 16.36 | 17.18 |
| | 3 | 39.83 | 41.25 | 18 | 18 | 14.72 | 14.72 |
| | 4 | 34.68 | 30.63 | 24 | 26 | 19.63 | 21.27 |
| | 5 | 44.25 | 41.57 | 17 | 18 | 13.91 | 14.72 |
| | 6 | 20.19 | 25.74 | 15 | 14 | 12.27 | 11.45 |
| | 7 | 25.22 | 22.12 | 20 | 21 | 16.36 | 17.18 |
| | 8 | 32.47 | 35.89 | 18 | 17 | 14.72 | 13.91 |
| | 9 | 41.56 | 47.34 | 19 | 19 | 15.54 | 15.54 |
| | 10 | 38.47 | 32.69 | 20 | 22 | 16.36 | 18 |
| Mean | | 34.98 | 34.12 | 20.00 | 20.30 | 16.36 | 16.61 |
| Standard deviation | | 7.02 | 7.23 | 3.74 | 3.80 | 3.06 | 3.11 |

Images of polymer particles combined with hyaluronic acid molecules according to the invention prepared according to example 2 are represented in FIG. 1b.

Results:

The release profile of the hyaluronic acid molecules combined with polymer particles prepared according to example 2 is represented in FIG. 4.

Example 3

Preparation of the Polymer Particles According to the Invention

A similar process to that of example 2 was employed in order to prepare polymer particles according to the invention. The only variation which is made with respect to the process of example 2 is the addition of a pharmaceutically acceptable excipient also having anti-inflammatory properties (trapper of free radicals), namely 1 ml of sorbitol in the form of a 10% by weight solution of sorbitol in ultrapure water, in place of the ultrapure water used in example 2.

Analysis of the Polymer Particles of the Invention According to Example 3:

The analyses were carried out on 6 batches of polymer particles according to the invention. The results obtained are as follows:
- size of the particles determined by polydispersity according to the particle size analysis using a Multisizer® 3 Coulter counter (Beckman Coulter): 31.15 μm±7.80 μm, and
- a content of hyaluronic acid charge of 13.94 μg of hyaluronic acid by mg of freeze-dried polymer particles.

TABLE 7

|  |  | Mean size (μm) After irradiation | Content of charge (μg/mg) After irradiation |
|---|---|---|---|
| Batches | 1 | 32.23 | 12.17 |
|  | 2 | 21.12 | 9.03 |
|  | 3 | 43.55 | 15.14 |
|  | 4 | 25.64 | 14.13 |
|  | 5 | 29.33 | 15.32 |
|  | 6 | 35.02 | 17.82 |
| Mean |  | 31.15 | 13.94 |
| Standard deviation |  | 7.80 | 3.02 |

Example 4

Preparation of the Polymer Particles According to the Invention

A similar process to that of example 1 was employed in order to prepare polymer particles according to the invention. The only variation which is made with respect to the process of example 1 is the addition of a pharmaceutically acceptable excipient also having anti-inflammatory properties (trapper of free radicals), namely 1 ml of sorbitol in the form of a 10% by weight solution of sorbitol in ultrapure water, in place of the ultrapure water used in example 1.

Analysis of the Polymer Particles of the Invention According to Example 4:

The analyses were carried out on 6 batches of polymer particles according to the invention. The results obtained are as follows:
- size of the particles determined by polydispersity according to the particle size analysis using a Multisizer® 3 Coulter counter (Beckman Coulter): 71.39 μm±7.70 μm, and
- a content of hyaluronic acid charge of 23.67 μg of hyaluronic acid by mg of freeze-dried polymer particles.

TABLE 8

|  |  | Mean size (μm) After irradiation | Content of charge (μg/mg) After irradiation |
|---|---|---|---|
| Batches | 1 | 65.82 | 23.61 |
|  | 2 | 72.37 | 25.57 |
|  | 3 | 63.92 | 22.19 |
|  | 4 | 85.17 | 26.03 |
|  | 5 | 67.61 | 22.73 |
|  | 6 | 73.45 | 21.91 |

TABLE 8-continued

|  | Mean size (μm) After irradiation | Content of charge (μg/mg) After irradiation |
|---|---|---|
| Mean | 71.39 | 23.67 |
| Standard deviation | 7.70 | 1.75 |

The invention claimed is:

1. Polymer particles consisting essentially of at least a poly(lactic-co-glycolic acid)-polyethylene glycol-poly(lactic-co-glycolic acid) (PLGA-PEG-PLGA) copolymer or a mixture of a poly(lactic-co-glycolic acid) (PLGA) polymer and a poly(lactic-co-glycolic acid)-polyethylene glycol-poly(lactic-co-glycolic acid) (PLGA-PEG-PLGA) copolymer, combined with hyaluronic acid molecules or hyaluronic acid salts via low-energy bonds and without formation of covalent bonds between the hyaluronic acid molecules or hyaluronic acid salts and the poly(lactic-co-glycolic acid)-polyethylene glycol-poly(lactic-co-glycolic acid) (PLGA-PEG-PLGA) copolymer or the poly(lactic-co-glycolic acid) (PLGA) polymer,
wherein the poly(lactic-co-glycolic acid)-polyethylene glycol-poly(lactic-co-glycolic acid) (PLGA-PEG-PLGA) copolymer has a molecular weight of between 50,000 g·mol$^{-1}$ and 70,000 g·mol$^{-1}$,
wherein said polymer particles continuously release the hyaluronic acid molecules or hyaluronic acid salts, and have a size ranging from 10 to 130 μm,
wherein the continuous release of the hyaluronic acid or hyaluronic acid salts continues to occur for between 8 to 12 weeks when the polymer particles are in synovial fluid, and
wherein the content by weight of hyaluronic acid or of hyaluronic acid salts combined with the polymer particles is in a range from 1 to 50 μg·mg$^{-1}$.

2. The polymer particles as claimed in claim 1, in which the low-energy bonds are at least one of hydrogen bonds and Van der Waals bonds.

3. The polymer particles as claimed in claim 1, consisting solely of poly(lactic-co-glycolic acid)-polyethylene glycol-poly(lactic-co-glycolic acid) (PLGA-PEG-PLGA) copolymer combined with the hyaluronic acid molecules or hyaluronic acid salts.

4. The polymer particles as claimed in claim 1, which are composed of the mixture of poly(lactic-co-glycolic acid) (PLGA) polymer and poly(lactic-co-glycolic acid)-polyethylene glycol-poly(lactic-co-glycolic acid) (PLGA-PEG-PLGA) copolymer.

5. The polymer particles as claimed in claim 4, in which the ratio by weight of the poly(lactic-co-glycolic acid) (PLGA) polymer to the poly(lactic-co-glycolic acid)-polyethylene glycol-poly(lactic-co-glycolic acid) (PLGA-PEG-PLGA) copolymer is in a range from 40/60 to 60/40.

6. The polymer particles as claimed in claim 1, in which the hyaluronic acid molecules have a molecular weight in a range from $0.8 \times 10^6$ to $1.2 \times 10^6$ g·mol$^{-1}$.

7. The polymer particles as claimed in claim 1, having a size ranging from 20 to 85 μm.

8. A composition comprising particles as claimed in claim 1 in suspension in an uptake solution.

9. The composition as claimed in claim 8, in which the uptake solution is an aqueous solution of hyaluronic acid or of hyaluronic acid salts, the concentration by weight of hyaluronic acid or of hyaluronic acid salts of which is in a range from 0.5 to 10%.

10. The composition as claimed in claim 8, further comprising a pharmaceutically or cosmetically acceptable excipient.

11. The composition as claimed in claim 8, further comprising another active principle.

12. A ready-for-use syringe, comprising a composition as defined in claim 8.

13. The polymer particles of claim 1, wherein no more than 50% of the hyaluronic acid or hyaluronic acid salts are released within 5 weeks when the polymer particles are in synovial fluid.

* * * * *